(12) United States Patent
Guy

(10) Patent No.: US 8,631,704 B2
(45) Date of Patent: Jan. 21, 2014

(54) FATIGUE TESTING DEVICE FOR WIND TURBINE BLADE TESTING, A METHOD OF TESTING WIND TURBINE BLADES AND A CONTROL SYSTEM FOR A BLADE TESTING ACTUATOR

(71) Applicant: Vestas Wind Systems A/S, Aarhus N (DK)

(72) Inventor: Stuart Guy, Lockerly (GB)

(73) Assignee: Vestas Wind Systems A/S, Aarhus N (DK)

( * ) Notice: Subject to any disclaimer, the term of this patent is extended or adjusted under 35 U.S.C. 154(b) by 0 days.

(21) Appl. No.: 13/763,341

(22) Filed: Feb. 8, 2013

(65) Prior Publication Data

US 2013/0213136 A1     Aug. 22, 2013

Related U.S. Application Data

(62) Division of application No. 12/602,387, filed as application No. PCT/EP2008/056685 on May 30, 2008, now Pat. No. 8,393,216.

(60) Provisional application No. 60/932,280, filed on May 30, 2007.

(30) Foreign Application Priority Data

May 30, 2007   (DK) .................................. 2007 00778

(51) Int. Cl.
 *G01M 3/00*   (2006.01)
(52) U.S. Cl.
 USPC .................................. 73/577; 73/579; 73/856

(58) Field of Classification Search
 USPC ............................. 73/597, 660, 577, 579, 602
 See application file for complete search history.

(56) References Cited

U.S. PATENT DOCUMENTS

| | | | | |
|---|---|---|---|---|
| 4,924,706 A | * | 5/1990 | Moore | 73/579 |
| 4,955,269 A | * | 9/1990 | Kendig et al. | 73/577 |
| 5,136,200 A | * | 8/1992 | Takizawa et al. | 310/323.16 |
| 5,445,027 A | * | 8/1995 | Zorner | 73/593 |
| 6,082,198 A | * | 7/2000 | Sabourin et al. | 73/633 |
| 6,102,664 A | * | 8/2000 | Nguyen | 416/248 |
| 6,240,792 B1 | * | 6/2001 | Elsesser | 73/865.9 |
| 6,441,571 B1 | * | 8/2002 | Ibuki et al. | 318/114 |
| 6,601,456 B1 | * | 8/2003 | Davidson et al. | 73/808 |
| 6,718,833 B2 | * | 4/2004 | Xie et al. | 73/812 |
| 6,732,591 B2 | * | 5/2004 | Miles et al. | 73/808 |
| 7,204,152 B2 | * | 4/2007 | Woodward et al. | 73/794 |
| 7,204,153 B2 | * | 4/2007 | Phipps | 73/808 |
| 7,953,561 B2 | * | 5/2011 | Musial et al. | 702/42 |
| 8,044,670 B2 | * | 10/2011 | Bjerge et al. | 324/650 |
| 2002/0017144 A1 | * | 2/2002 | Miles et al. | 73/808 |
| 2006/0037402 A1 | * | 2/2006 | Musial et al. | 73/664 |

* cited by examiner

*Primary Examiner* — Peter Macchiarolo
*Assistant Examiner* — Samir M Shah
(74) *Attorney, Agent, or Firm* — Wood, Herron & Evans, LLP

(57) ABSTRACT

The invention provides a fatigue exciter for wind turbine blades. Wind turbine blades require excitation at or near their natural frequency to induce bending moments that simulate in service loadings and must be easily controllable and with the minimum of unnecessary added mass or force. The invention provides a device and a method by which force controlled feedback is used for finding an optimal excitation frequency. This force could be provided e.g. by a digital signal generator.

21 Claims, 2 Drawing Sheets

FATIGUE TESTING DEVICE FOR WIND TURBINE BLADE TESTING, A METHOD OF TESTING WIND TURBINE BLADES AND A CONTROL SYSTEM FOR A BLADE TESTING ACTUATOR

CROSS-REFERENCE TO RELATED APPLICATIONS

The present application is a divisional of U.S. patent application Ser. No. 12/602,387 filed Feb. 4, 2010 now U.S. Pat. No. 8,393,216 which is a U.S. national phase application of PCT/EP2008/056685 filed May 30, 2008 which designates the United States and claims the benefit of 60/932,280 filed May 30, 2007. Each of these applications is incorporated by reference herein in its entirety.

TECHNICAL FIELD

The invention relates to a testing device for fatigue testing of wind turbine blades. The testing device comprises a bench for fixation of a blade and an actuator adapted to apply a cyclic load on the blade. The invention further relates to a method of testing blades and to a controller for controlling a blade testing actuator.

BACKGROUND OF THE INVENTION

Wind turbines for producing electricity typically use slender turbine blades extending radially from a hub. The hub is mounted to a shaft which drives a generator. Wind turbines are made larger and larger, and the static and dynamic loads on the turbine blades therefore increase.

In blade testing, static loads may be useful for evaluating stiffness and ultimate strength of a turbine blade. However, in practice, the load on a wind turbine blade varies constantly and to evaluate fatigue resistance of the blade, a cyclical load may be applied in large test facilities.

For economical reasons, it is desired to reduce the duration of a test. Typically, however, it is expensive and difficult to deflect the very large blades at large amplitudes and frequencies, and today several months are expected for each blade test.

During a typical test, a heavy load rotates eccentrically. The load is strapped to the blade at a location between the hub end and the tip end of the blade and therefore makes the blade oscillate. Unfortunately, the rotating mass increases the mass of the deflecting system, and the lowest resonance frequency is therefore reduced, and the duration of the test therefore increases further.

SUMMARY OF THE INVENTION

To improve blade testing, the invention provides a fatigue testing device for wind turbine blade testing. The device comprises an actuator adapted to deflect the blade at an excitation frequency and a control system adapted to find a natural frequency for the blade and to set the excitation frequency to the natural frequency. Since the control system is adapted to find the natural frequency and to deflect the blade at this frequency, the duration of the test and the use of energy for the test can be optimized.

The control system may be adapted to find the natural frequency by modulation of the excitation frequency, and it may further be adapted, during modulation of the excitation frequency, to provide an input signal significant for an increase or decrease of an input force necessary to deflect the blade and to provide an output signal significant for an amplitude of the deflection. Since the device is capable of determining increase or decrease in input force while modulating the frequency, the excitation frequency can be selected in order to optimize duration of the test and/or in order to optimize the energy costs of the test.

Accordingly, the device may further be adapted to determine a ratio between the input force and the amplitude, and to select an excitation frequency based on the ratio.

As an example, the device may be adapted to select an excitation frequency which provides a minimal input force relative to the amplitude.

The frequency could be modulated by a digital sine wave generator controlled by a PC.

The input force could be provided in several different ways. One way is by arranging a strain sensitive structure, e.g. a strain gauge, a fiber optic or similar means between the actuator and the blade or at different locations on the actuator and/or on the blade. When the blade is deflected, the strain sensitive structure provides a signal representing the force by which the actuator influences the blade. Another way is to measure the amount of energy which is consumed by the actuator during deflection of the blade. Yet another way is to measure deflection of a link between the blade and the actuator.

The signal from the strain sensitive structure or similar signal representing the force which is necessary to make the blade deflect can be sampled in a period of time in which the frequency is modulated. By relating the frequencies to the sampled input forces, it can be determined at which frequency least input force is necessary.

The amplitude could be determined e.g. by an optical sensor e.g. a camera, or the amplitude could be determined by measuring deflection of the blade via strain sensitive structures which are attached to the blade. The amplitude could be sampled in a period of time in which the frequency is modulated, and by relating the frequencies to the sampled amplitudes, it can be determined at which frequency a maximum amplitude is obtained.

The amplitude and the input force signal could be sampled simultaneously, and both samples may be taken into consideration when selecting a suitable frequency for testing a blade. As an example, it may be determined if a maximum deflection and a minimum force are obtainable at one and the same frequency, and in that case, that frequency may be chosen for the test. This could be achieved by manually increasing and decreasing the frequency slightly and observing the change in the amplitude.

The most efficient excitation frequency would normally be at, or near a natural frequency of the blade. To induce bending moments that simulate in service loadings, this frequency is typically superior for testing purposes. In order to obtain a highest possible natural frequency, the weight of the tested object can advantageously be kept at the level of the weight of the blade itself without attaching any weight increasing elements thereto. The device may comprise an assembly bench for fixation of a blade and an actuator adapted to convert an input force to a cyclic load, the actuator being supported externally without weighing down the blade. This may be obtained by placing the actuator on the ground in the vicinity of the blade so that the blade does not carry the weight of the actuator. The force could be applied to the blade either directly from the actuator or through a lever arrangement. In this way, the actuator is arranged not to influence the natural frequency of the tested object.

The actuator could e.g. be electrically, hydraulically or pneumatically driven, and it could include a rotating member with an eccentrically attached mass or lever arm. To avoid an excessive load and possible damage to the blade which may occur upon repeated punching contact, the actuator is preferably in constant contact with the blade. As an example, the actuating part of the actuator could be bolted, strapped or otherwise fastened to the blade while the remaining part of the actuator is bolted or otherwise fastened to the ground. The interface between the actuator and the blade may therefore include bolts, straps, belts or any kind of fixtures. With the above-mentioned weight-considerations in mind, the interface may preferably have a weight which is either carried entirely by the actuator and not by the blade, or the weight may be very low compared to the weight of the blade, e.g. below 1 percent of the weight of the blade or even below 0.1 percent of the weight of the blade itself.

The device may comprise a set of strain sensitive structures which can be fixed to the blade at different locations along the blade. The strain sensitive structures can be used for determining a deflection of the blade, e.g. for determining the amplitude of the deflection, or the strain sensitive structures can be used for determining a general condition of the blade, e.g. to observe changes in the blade throughout the fatigue testing. The signals from the strain sensitive structures are collected and used in a frequency modulation algorithm.

The frequency modulation may comprise the following steps:

An approximation of the natural frequency is selected manually in the first instance.

The control system continuously modulates the frequency by a small amount above and below the selected frequency.

The control system monitors the amplitude from the strain sensitive structures and compares this with the mean force input and calculates the efficiency.

The selected frequency is then reset to the value that gives the highest efficiency. In this way, the frequency of operation moves toward the most efficient operating condition automatically for varying conditions.

A separate control loop running concurrently ensures the amplitude of the strain is maintained at the level required for the test.

The frequency algorithm delivers control signals for amplitude and frequency modulation control. The control signal could be in the form of voltages proportional to amplitude and frequency as inputs to the digital sine wave generator.

The signal is received e.g. by a digital signal generator which in response generates a signal to control the actuator, e.g. an on/off signal or a proportional signal for a valve which controls a flow of a fluid under pressure to a hydraulic actuator.

To enable variations in the resonance frequency of the blade, the blade may further be confined or fixed at different locations along the blade. As an example, the testing may be interesting particularly with respect to a tip end of the blade. By fixing the blade to the bench, floor or any other surrounding obstacle at a location between the hub end and tip end of the blade, the tip end of the blade may oscillate faster, and the duration of the test can be decreased further. Accordingly, the device may comprise at least one fixation means which is adjustable to allow fixation of the blade to a surrounding object at different locations along the blade.

The device may comprise an additional actuator adapted to deflect the blade at an excitation frequency which could be equal to the frequency of the previously mentioned actuator or which could be different from the excitation frequency of the previously mentioned actuator. At least one of the actuator and the additional actuator could be adjustably positioned along the blade so that at least one of the actuators can be arranged to cause deflection at different points along the blade. Accordingly, one of the actuators could be fixed relative to the blade and the other one of the actuators could be arranged freely along the blade and cause deflection at the same or at a different frequency at another location along the blade.

In fact, the device may comprise any number of fixtures for fixing the blade to a surrounding object, e.g. to the floor of the test area, and any number of actuators arranged to deflect the blade at different locations along the blade.

In a second aspect, the invention provides a method of testing a wind turbine blade, the method comprising the steps of:

fixing a blade to a bench,
providing an input force for operating the actuator to apply, at an excitation frequency, a cyclic load to the blade at a location at a distance from the hub end,
modulating the excitation frequency and input force,
determining an amplitude of the movement of the blade, and
selecting an excitation frequency based on a ratio between the input force and the amplitude.

The method may in particular comprise the step or steps of repeatedly modulating the frequency and subsequently re-selecting the excitation frequency during a test. This is in order to take changes to the natural frequency of a blade into consideration, and for test with a long duration, this may be important for the test result as well as the economy of the test.

The blade could be fixed to the bench by any kind of fixation means, and at any location along the blade. However, it may typically be desired to fix a hub end of the blade to the bench, and it may even be desired not only to fixate the blade to the bench, but to fixate the hub of the wind turbine to the bench and the fixate the blade to the hub. In this way, not only the blade but also the interface between the blade and the hub can be tested.

Again, to enable variations in the resonance frequency of the blade, the blade may further be confined or fixed at different locations along the blade.

In a third aspect, the invention provides a control system for controlling a testing device for wind turbine blades, the testing device comprising an actuator, the control system being adapted to modulate an excitation frequency at which the actuator applies a load to the blade, to modulate an input force provided for the actuator to apply the load to the blade, to determine an amplitude of movement of the blade and to select an excitation frequency based on a ratio between the input force and the amplitude. The invention may be implemented in a software product for execution on a regular PC via a standard interface to a servo-amplifier or by similar interface to the actuator.

The device and method may in fact be applied for testing blades not only for wind turbines but also for testing propeller blades for ventilators, ships etc.

DETAILED DESCRIPTION

Figure 1:
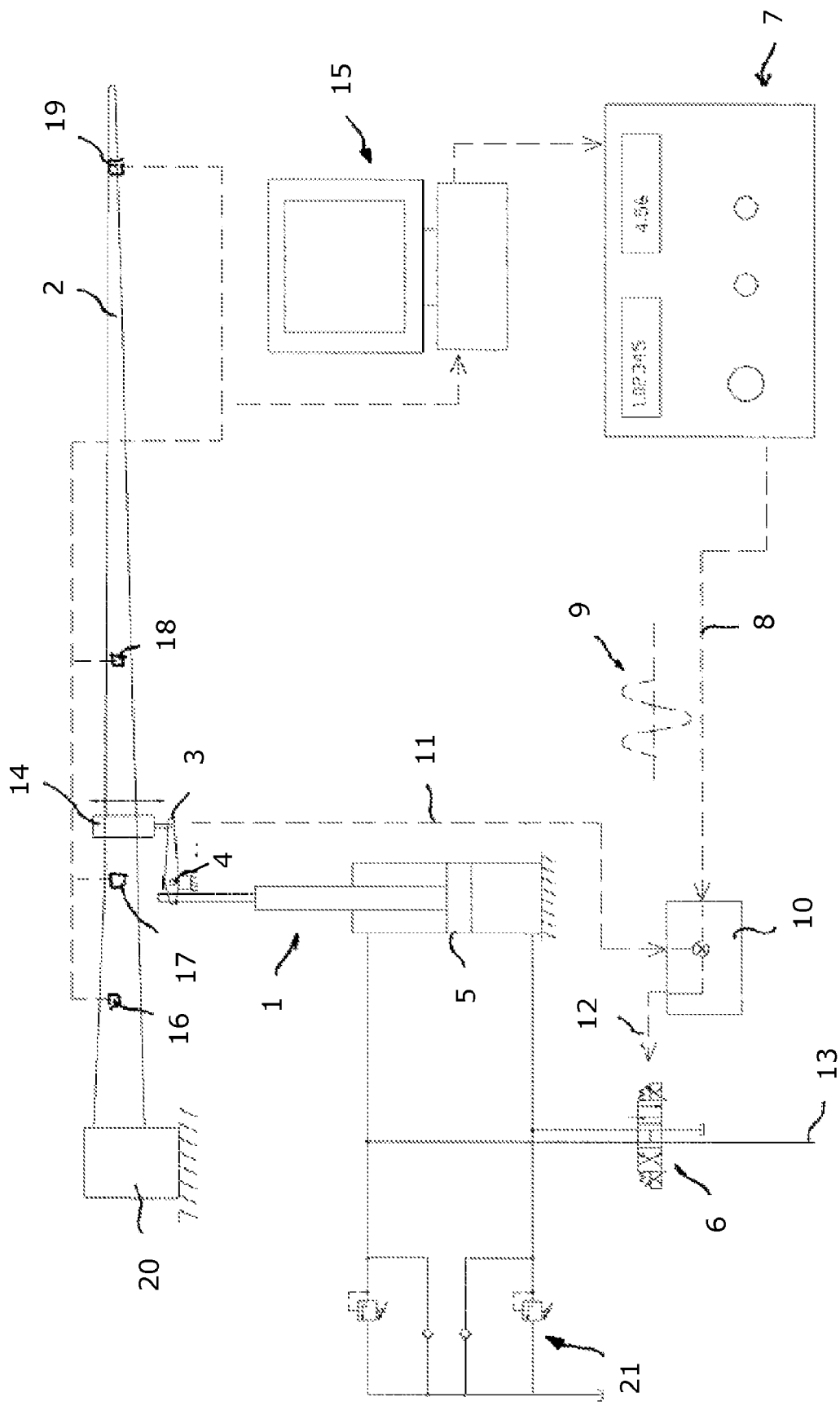
FIG. 1 illustrates a fatigue exciter according to the invention.

FIG. 1 illustrates schematically a fatigue exciter according to the invention. The system comprises a proportional force controlled feedback such that the blade is excited by a sinusoidal force to match the natural excitation frequency of the blade. The exciter comprises an actuator 1 adapted to deflect the blade 2. The actuator comprises a lever arm 3 rotatable around a pivot point 4 under influence of a sinusoidal force from the hydraulic cylinder 5. The sinusoidal force is controlled via the valve 6 by a digital signal generator 7 via a servo amplifier 10.

The digital signal generator generates a control signal which is transmitted via the communication path 8, e.g. constituted by a cable, or a wireless path. The control signal is a sine-shaped signal as depicted, c.f. numeral 9. The control signal is received by the servo amplifier 10. The servo amplifier 10 also receives an input force signal indicating the force on the lever arm 3 via the communication path 11. Based on the control signal and the input force signal, the servo amplifier 10 provides an instruction signal which is communicated to the valve 6 via the communication path 12. The valve receives a hydraulic fluid under pressure via conduit 13 and provides the fluid to the actuator 1 based on the instruction signal.

The lever arm 3 and the cylinder 5 are both placed on the ground and they interact with the blade via a connection member 14. The weight of the connection member is carried by the actuator, and the actuator arrangement including the connection member 14 therefore adds no additional weight to the blade.

The digital signal generator 7 is controlled either manually or more effectively by a PC based Data Acquisition system 15. The PC receives signals from the strain gauges 16, 17, 18 and 19, and varies the force amplitude to achieve the desired strain levels required for the test. The Data Acquisition system 15 also controls the frequency of the digital signal generator 7 to match the natural frequency of the blade. This is achieved by modulating the output frequency up and down and then comparing the resulting input force needed to maintain the amplitude.

The blade itself is fixed in a bench 20 which is carried on the ground, preferably separated from the support of the actuator 1.

Due to aerodynamic damping and temperature effects, the natural frequency may change during a test. By modulating the frequency repeatedly during a test and by selecting each time a new optimal frequency, the device becomes capable of maintaining, throughout a test which may take several months, a most efficient excitation value. The effect of the two adjustments (amplitude and frequency) is compensated for within the software algorithm to achieve the desired level of control.

The PC can also be easily programmed to automatically vary the strain levels for different numbers of cycles to better match the fatigue cumulative damage of the blade being tested.

The system further comprises a pressure relief and anti-cavitations valve arrangement 21 at a discharge end of the conduit system.

Figure 2:
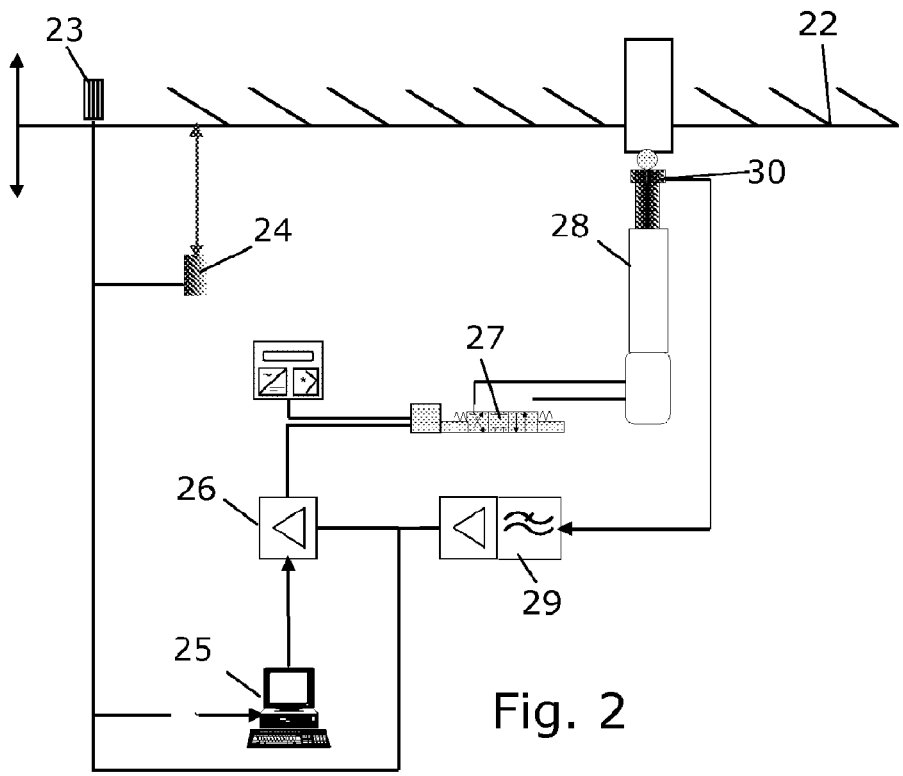
FIGS. 2-4 illustrate further details of an example of a control system for operating the blade fatigue exciter according to the invention.
Figure 3:
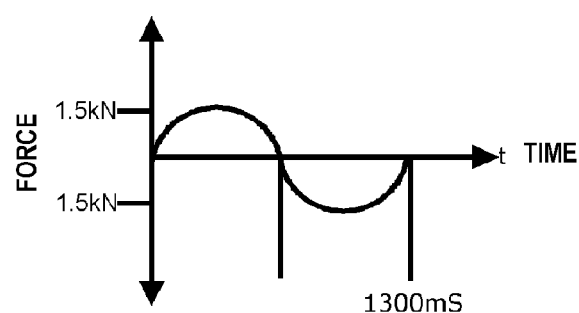
Figure 4:
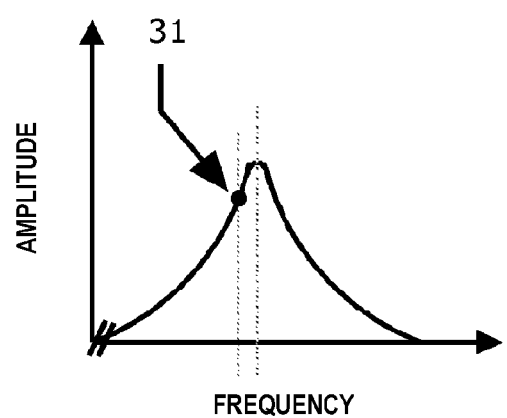

FIGS. 2-4 illustrate further details of an example of a control system for operating the blade fatigue exciter. The system uses a proportional hydraulic system to input a sinusoidal load close to the blades natural frequency ($\omega n$).

As illustrated in FIG. 2, the system comprises the blade under test 22, stain gauges 23 and/or a laser displacement sensor 24. The sensors are connected to a computer 25 which again controls a PID controller 26. The computer can be a regular PC with labview as controller. The PID controller is connected to a proportional valve 27 which controls a hydraulic flow to and from the actuator 28.

The lowpass filter and amplifier 29 returns a load signal from the loadcell 30.

A closed loop PID control module is used in conjunction with a load cell to ensure that load application follows the drive demand sinusoidal profile which is illustrated in FIG. 3.

A second loop controls applied load range by comparing the summation of strain gauges or displacement lasers against a target bending moment.

Initially the control system brings the blade under test up to load at just under the blades recorded natural frequency. Typically this is in the size of 0.98 $\omega n$, as determined by a pre-test frequency sweep where the frequency is varied over an interval which includes the natural frequency. This is illustrated by the arrow 31 in the graph in FIG. 4. FIG. 4 illustrates the frequency of operation along the abscissa and the attenuation along the ordinate.

Having $\omega o$ offset from $\omega n$ allows the controller to know which slope it is operating on, eliminating system hunting. It can therefore adjust the $\omega o$ with shifts in $\omega n$ which occur with changes to the blades structure, damping and temperature. This again utilizes a PID loop within the software of the PC to make adjustments, increasing $\omega o$ when load decreases, and visa versa. The system can therefore track $\omega n$ through the complete test.

What is claimed is:

1. A fatigue testing device for a wind turbine blade, the blade having a hub end and a tip end and a longitudinal axis, the device comprising:
    a ground supported bench configured to have the hub end of the blade operably fixed thereto such that the blade is cantilevered therefrom, and
    a ground supported actuator spaced from said bench and configured to be connected to the blade at a position between the hub end and the tip end of the blade,
    said bench and said actuator configured to support the blade such that the longitudinal axis of the blade is in a generally horizontal attitude,
    said actuator configured to reciprocatingly translate the blade at an excitation frequency in a direction generally perpendicular to the longitudinal axis of the blade and generally normal to the ground, said actuator configured to be attached to the blade in such a manner that the structural dynamics characteristics of the blade cantilevered from said bench and with said actuator attached thereto are substantially the same as they would be were the blade only cantilevered from said bench.

2. The fatigue testing device of claim 1 further including a control system configured to find an initial natural frequency of the blade and to set the excitation frequency to the initial natural frequency, said control system further configured to find a subsequent changed natural frequency of the blade and to set the excitation frequency to the subsequent changed natural frequency.

3. The fatigue testing device of claim 2 wherein said control system is configured to find the subsequent changed natural frequency of the blade by modulating the excitation frequency so that the excitation frequency is repeatedly swept forwards above and backwards below the initial natural frequency, and during modulation of the excitation frequency, monitoring blade amplitude and an input force of said actuator necessary to produce a desired blade amplitude, and if the necessary input force decreases during forward sweeping of the excitation frequency to continue forward sweeping of the excitation frequency, and if the necessary input force increases during forward sweeping of the excitation frequency to cause backward sweeping of the excitation frequency.

4. The fatigue testing device of claim 3 wherein said control system is configured to modulate the excitation frequency so that the excitation frequency is continuously swept forwards above and backwards below the initial natural frequency of the blade.

5. The fatigue testing device of claim 1 further comprising a first sensor configured to sense an input force to the blade from said actuator, a second sensor configured to sense an amplitude of deflection of the blade due to said actuator, and a control system in communication with said actuator and said first and second sensors, said control system including a controller.

6. The fatigue testing device of claim 5 wherein said control system is configured to monitor the amplitude of the blade as sensed by said second sensor, to find an initial natural frequency of the blade based on the amplitude of the blade sensed by said second sensor, and to set the excitation frequency of said actuator to the initial natural frequency.

7. The fatigue testing device of claim 6 wherein said control system further includes a frequency modulation algorithm and is further configured to modulate the excitation frequency so that the excitation frequency is repeatedly swept forwards above and backwards below the initial natural frequency.

8. The fatigue testing device of claim 7 wherein said control system is configured to find a subsequent natural frequency to set the excitation frequency to by, during modulation of the excitation frequency, monitoring blade amplitude via said second sensor and the input force of said actuator necessary to produce a desired blade amplitude via said first sensor, and if the necessary input force decreases during forward sweeping of the excitation frequency, to continue forward sweeping of the excitation frequency, and if the necessary input force increases during forward sweeping of the excitation frequency, to cause backward sweeping of the excitation frequency.

9. The fatigue testing device of claim 8 wherein the control system is further configured, during modulation of the excitation frequency, to provide an input signal significant of an increase or decrease of the input force necessary to deflect the blade and to provide an output signal significant of the amplitude of the deflection and further configured to select a subsequent excitation frequency based on the input signal, the output signal, or a ratio therebetween.

10. The fatigue testing device of claim 8 wherein the control system is further configured, during modulation of the excitation frequency, to provide an input signal significant of an increase or decrease of the input force necessary to deflect the blade and to provide an output signal significant of the amplitude of the deflection and further configured to select a subsequent excitation frequency based on a ratio between the input force and the amplitude, the input signal, or the output signal, wherein the selection facilitates a minimal ratio between the input force and the amplitude.

11. The fatigue testing device of claim 8 further comprising at least one strain sensitive structure being attachable to the blade, said device being further configured to modulate the excitation frequency based on a signal generated by said strain sensitive device.

12. The fatigue testing device of claim 8 further comprising an additional actuator configured to deflect the blade at an additional excitation frequency.

13. The fatigue testing device of claim 12 wherein the additional excitation frequency is adjustable.

14. The fatigue testing device of claim 12 wherein the additional excitation frequency is adjustable independent of the excitation frequency.

15. The fatigue testing device of claim 8 further comprising an additional fixture for fixing a second portion of the blade.

16. The fatigue testing device of claim 15 wherein said additional fixture is adjustable to allow fixation at different locations along the blade.

17. The fatigue testing device of claim 8 further comprising at least one optical sensor, said control system being further configured to modulate the excitation frequency based on a signal generated by said optical sensor.

18. The fatigue testing device of claim 8 further comprising at least one laser displacement sensor, said control system being further configured to modulate the excitation frequency based on a signal generated by said laser displacement sensor.

19. The fatigue testing device of claim 8 wherein said control system is further configured to modulate the excitation frequency so that the excitation frequency is continuously swept forwards above and backwards below the initial natural frequency of the blade.

20. The fatigue testing device of claim 6 wherein said control system is configured to bring the blade under test up to an initial load at a frequency within 10 percent under the initial natural frequency.

21. The fatigue testing device of claim 20 wherein the initial natural frequency is determined by a pre-test frequency sweep.

* * * * *